US005591716A

United States Patent [19]
Siebert et al.

[11] Patent Number: 5,591,716
[45] Date of Patent: Jan. 7, 1997

[54] BENEFICIAL WOUND HEALING APPLICATIONS OF CALRETICULIN AND OTHER HYALURONAN-ASSOCIATED PROTEINS

[75] Inventors: John W. Siebert, New York, N.Y.; Hari G. Garg, Belmont, Mass.; Leslie I. Gold, New York, N.Y.

[73] Assignees: New York University, New York, N.Y.; The General Hospital Corp., Boston, Mass.

[21] Appl. No.: 155,933

[22] Filed: Nov. 19, 1993

[51] Int. Cl.$^6$ ............................ A61K 38/16; A61K 38/18
[52] U.S. Cl. ............................ 514/12; 530/350; 530/395; 530/399
[58] Field of Search ............................ 514/12; 530/350, 530/399, 395

[56] References Cited

U.S. PATENT DOCUMENTS

| | | | |
|---|---|---|---|
| 4,141,973 | 2/1979 | Balazs | 424/180 |
| 5,124,392 | 6/1992 | Robertson et al. | 524/427 |
| 5,166,331 | 11/1992 | della Valle et al. | 536/55.1 |
| 5,310,728 | 5/1994 | Shimizu et al. | 514/12 |

OTHER PUBLICATIONS

Adzick, N. S. et al., "Comparison of Fetal, Newborn, and Adult Wound Healing by Histologic, Enzyme–Histochemical, and Hydroxyproline Determinations", (1985) *J Ped Surg* 20:315–319.

DePalma, R. L. et al., "Fetal Wound Matrix is Composed of Proteoglycan Rather Than Collagen", (1987) *Surg Forum* 38:626–628.

DePalma, R. L. et al., "Characterization and Quantitation of Wound Matrix in the Fetal Rabbit", (1989) *Matrix* 9:224–231.

Longaker, M. T. et al., "Studies in Fetal Wound Healing", (1989) *Ann Surg* 210:667–672.

Laurent, T. C., "Biochemistry of Hyaluronan", (1987) *Acta Otolaryngol* 442 (*Suppl*): 7–24.

Abatangelo, G. et al., "Healing of Hyaluronic Acid–Enriched Wounds: Histological Observations", (1983) *J Surg Res* 35:410–416.

Michalak, M. et al., "Calreticulin", (1992) *Biochem J* 285:681–692.*

Siebert, J. W. et al., "Fetal Wound Healing: A Biochemical Study of Scarless Healing", (1990) *Plast Reconstr Surg* 85:495–502.

Bakshandeh, N. et al., "Isolation and Partial Characterization of Hyaluronan–Protein–Collagen Complex (HA–PC) From Fetal Sheep Skin of Different Gestational Ages", (1992) *Biochem Intl* 28:843–851.*

Burd, D. A. R. et al., "Human Skin and Post–Burn Scar Hyaluronan: Demonstration of the Association with Collagen and other Proteins", (1989) *Matrix* 9:322–327.

Burd, D. A. R. et al., "Hyaluronan and Wound Healing: A New Perspective", (1991) *Brit. J. Plast. Surg.* 44:579–584.

Burd, D. A. R. et al., "Hyaluronan–Protein Interactions", (1992) In: Adzick et al., eds., Fetal Wound Healing, Elsevier, New York, 1992, pp. 199–214.

Shah, M. et al., "Control of Scarring in Adult Wounds by Neutralising Antibody to Transforming Growth Factor β", (1992) *Lancet* 339:213–214.

Krummel, T. M. et al., "Transforming Growth Factor Beta (TGF–β) Induces Induces Fibrosis in a Fetal Wound Model", (1988) *J. Ped Surg* 23:647–652.

Davidson, J. M. et al., Clin. Mater. vol. 8, Nos. 1–2, pp. 171–177, 1991.

Bakshandeh, N. et al., Biochem. Int., vol. 28(5), pp. 843–851, 1992.

Ten Dijke et al., Biotechnology, vol. 7, pp. 793–798, 1989.

Michalak, Marek et al, Biochem J., vol. 285, pp. 681–692, 1992.

Opas, Michal et al., Biochem. Cell. Biol., vol. 70, pp. 972–979, 1992.

Estes, J. M. et al., J. Pediatr. Surg., vol. 28, No. 10 pp. 1227–1231, 1993.

Bleacher, J. C. et al., Dermatol. Clin., vol. 11(4), pp. 677–683, 1993.

Wadstrom, J. et al., Upsala Jour. of Med. Sciences, vol. 98(2), pp. 159–167, 1993.

Mast, B. A. et al., Matrix, vol. 11(1), pp. 63–68, 1991.

Siebert, J. W. et al., Plast. Reconstr. Surg., vol. 85(4), pp. 495–504, 1990.

Burgess et al., J. Cell Biol., vol. 111, pp. 2129–2138, 1990.

Lazar et al., Mol. & Cell Biol., vol. 8(3), pp. 1247 to 1252, 1988.

*Primary Examiner*—Chhaya D. Sayala
*Attorney, Agent, or Firm*—Morrison & Foerster LLP

[57] ABSTRACT

Hyaluronan associated proteins, in particular calreticulin, promote the accelerated and relatively scarless healing of wounds. Methods for treating wounds using such proteins, and pharmaceutical compositions comprising such proteins, are provided.

14 Claims, 4 Drawing Sheets

INCISIONAL WOUNDS

| ISOFORM OF TGF B | NO WOUND 1 2 3 | DAY 1 1 2 3 | DAY 5 1 2 3 | DAY 7 1 2 3 | DAY 10 1 2 3 | DAY 14 1 2 3 | DAY 21 1 2 3 |
|---|---|---|---|---|---|---|---|
| EPIDERMIS: | | | | | | | |
| STRATUM CORNEUM | 3 0 3 | 3 1 0 | 3 0 0 | 3 3 1 | 2 2 0 | 2 0 1 | 2 0 1 |
| STRATUM GRANULOSUM | 2 2 2 | 1 2 2 | 0 2 2 | 1 3 2 | 0 2 1 | 1 2 2 | 1 2 2 |
| STRATUM SPINOSUM | 1 1 2 | 1 2 1 | 1 1 1 | 1 2 1 | 0 0 1 | 0 2 1 | 1 1 2 |
| STRATUM BASALIS | 1 2 2 | 0 1 2 | 1 1 2 | 0 1 2 | 0 0 2 | 0 0 2 | 0 1 2 |
| MIGRATING EPIDERMIS | NA | 1 1 1 | 1 1 NA | 1 1 NA | 1 1 NA | 1 1 NA | 1 1 NA |
| GRANULATION TISSUE | NA | 2 2 2 | 1 1 NA | 1 1 NA | 1 1 NA | 1 1 NA | 1 1 NA |
| DERMIS* | 0 1 2 | 1 1 2 | 1 1 3 | 1 1 2 | 1 1 2 | 0 1 2 | 0 1 2 |
| HAIR FOLLICLES | 1 2 2 | 1 1 2 | 2 1 2 | 1 1 3 | 1 1 2 | 1 2 2 | 1 1 2 |
| MEROCRINE GLANDS | 2 2 1 | 2 2 3 | 1 2 3 | 1 2 3 | 2 3 3 | 1 2 3 | 0 0 2 |
| SEBACEOUS GLANDS | 1 2 2 | 2 3 3 | 1 2 3 | 1 2 3 | 1 2 3 | 1 2 3 | 0 1 2 |
| ENDOTHELIAL CELLS | 0 1 0 | 1 2 3 | 1 1 3 | 1 2 2 | 1 2 2 | 1 1 2 | 1 1 2 |

*Dermis adjacent to wound
0=no immunostaining, 1=mild immunostaining
2=moderate immunostaining, 3=intense immunostaining
NA=not applicable

FIG. 1

EXCISIONAL WOUNDS

| ISOFORM OF TGF B | NO WOUND 1 | NO WOUND 2 | NO WOUND 3 | DAY 1 1 | DAY 1 2 | DAY 1 3 | DAY 2 1 | DAY 2 2 | DAY 2 3 | DAY 5 1 | DAY 5 2 | DAY 5 3 | DAY 7 1 | DAY 7 2 | DAY 7 3 | DAY 10 1 | DAY 10 2 | DAY 10 3 | DAY 14 1 | DAY 14 2 | DAY 14 3 | DAY 21 1 | DAY 21 2 | DAY 21 3 |
|---|---|---|---|---|---|---|---|---|---|---|---|---|---|---|---|---|---|---|---|---|---|---|---|---|
| EPIDERMIS: | | | | | | | | | | | | | | | | | | | | | | | | |
| STRATUM CORNEUM | 3 | 0 | 2 | 3 | 1 | 1 | 3 | 0 | 0 | 3 | 1 | 1 | 3 | 1 | 1 | 3 | 1 | 0 | 3 | 1 | 1 | 3 | 0 | 2 |
| STRATUM GRANULOSUM | 2 | 2 | 2 | 2 | 3 | 3 | 2 | 3 | 2 | 2 | 3 | 3 | 2 | 3 | 3 | 2 | 3 | 3 | 2 | 3 | 3 | 1 | 2 | 2 |
| STRATUM SPINOSUM | 1 | 1 | 2 | 2 | 3 | 3 | 2 | 3 | 3 | 2 | 3 | 3 | 2 | 3 | 3 | 2 | 3 | 3 | 1 | 3 | 3 | 1 | 2 | 2 |
| STRATUM BASALIS | 1 | 2 | 2 | 2 | 3 | 3 | 2 | 2 | 3 | 1 | 3 | 3 | 2 | 3 | 3 | 2 | 3 | 3 | 1 | 3 | 3 | 1 | 2 | 2 |
| MIGRATING EPIDERMIS | NA | NA | NA | 1 | 1 | 1 | 0 | 0 | 0 | 0 | 0 | 0 | NA | NA | NA | NA | NA | NA | NA | NA | NA | NA | NA | NA |
| GRANULATION TISSUE | NA | NA | NA | 2 | 2 | 2 | 3 | 3 | 3 | 2 | 3 | 3 | NA | NA | NA | NA | NA | NA | NA | NA | NA | NA | NA | NA |
| DERMIS* | 0 | 1 | 2 | 1 | 2 | 2 | 2 | 2 | 2 | 2 | 3 | 3 | 1 | 1 | 2 | 1 | 1 | 2 | 1 | 1 | 2 | 0 | 1 | 2 |
| HAIR FOLLICLES | 1 | 2 | 2 | 2 | 3 | 3 | 3 | 3 | 3 | 2 | 3 | 3 | 2 | 3 | 3 | 2 | 3 | 3 | 1 | 3 | 3 | 1 | 2 | 2 |
| MEROCRINE GLANDS | 2 | 2 | 1 | 2 | 2 | 2 | 1 | 3 | 3 | 1 | 2 | 2 | 1 | 2 | 3 | 2 | 3 | 3 | 1 | 2 | 3 | 0 | 0 | 2 |
| SEBACEOUS GLANDS | 1 | 2 | 2 | 2 | 3 | 3 | 1 | 2 | 2 | 1 | 2 | 3 | 1 | 2 | 3 | 1 | 2 | 3 | 1 | 2 | 3 | 0 | 1 | 2 |
| ENDOTHELIAL CELLS | 0 | 1 | 0 | 2 | 2 | 3 | 2 | 3 | 3 | 1 | 2 | 3 | 1 | 2 | 2 | 1 | 2 | 3 | 1 | 2 | 2 | 0 | 1 | 1 |

*Dermis adjacent to wound
0=no immunostaining, 1=mild immunostaining
2=moderate immunostaining, 3=intense immunostaining
NA=not applicable

FIG. 2

BENEFICIAL WOUND HEALING APPLICATIONS OF CALRETICULIN AND OTHER HYALURONAN-ASSOCIATED PROTEINS

BACKGROUND OF THE INVENTION

1. Field of the Invention

The present invention in the field of medicine relates to novel compositions and methods for the treatment of wounds and for the promotion of more rapid wound healing with diminished scarring.

2. Description of the Background Art

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation.

Healing wounded tissue is among the most essential, dramatic and visible jobs performed by the body. Significant progress has recently been made in understanding the sequence of events occurring when traumatized tissue heals. Several dozen different growth factors, or cytokines, have been identified that participate in healing. These growth factors signal the blood to coagulate and plug the gap, they attract immune cells to fight infiltrating microorganisms, and ultimately promote neighboring skin cells to cover the wound. If the wound is sufficiently large, these factors stimulate production of new skin, new blood vessels, new supporting connective tissue and even new bone.

Adult Wound Healing

Adult wound healing in response to injury results in restoration of tissue continuity (Adzick N. S. et al. (eds), *FETAL WOUND HEALING*, Elsevier, New York 1992, Chapters 1–3, 12, 13 and references cited therein). While some amphibians heal by regeneration, adult mammalian tissue repair involves a complex series of biochemical events that ultimately ends in scar formation. The events occurring during wound repair resemble the process of development, including synthesis, degradation and resynthesis of the extracellular matrix (ECM) (Smith L. T. et al. (1982) *J Invest Dermatol* 79:935–1045; Blanck C. E. et al. (1987) *J Cell Biol* 105:139(A)). The ECM contains several macromolecules, including collagen, fibronectin, fibrin, proteoglycans, and elastin (Cohen J. K. et al. (1983) *BIOCHEMISTRY AND PHYSIOLOGY OF THE SKIN*. New York: Oxford University Press, pp 462–470, 1983; Alvarez O. M., In: *CONNECTIVE TISSUE DISEASE: MOLECULAR PATHOLOGY OF THE EXTRACELLULAR MATRIX*, Uitto J. et al., eds, New York: Marcell Decker, pp. 367–384, 1986; Murphy-Ullrich J. E. et al., supra, at pp. 455–473). When the injury involves the dermis, repair also entails the removal of cellular debris (Grinnel F. et al. (1981) *J Invest Dermatol* 76:181–189) and the laying down of a new ECM over which epidermal continuity can be reestablished. This process of repair and dermal matrix reorganization is manifested as scar formation and maturation.

Microscopically, the scar can be identified by its abnormal organization of cellular and matrix elements when compared to surrounding uninjured skin. Grossly, normal scars progress towards stability and maturity. An immature scar is raised, red, and firm, whereas a mature scar is flat, white, and soft. However, not all healing follows this pattern and can result in abnormal scars, such as hypertrophic or keloid scars. Both of these types of scars can be differentiated clinically and histomorphologically from normal scar, but this invariably involves repeated observation over a period of time, as hypertrophic scars in particular can progress to the maturity of a normal scar albeit over a much longer time course.

Adult wound repair includes the stages of hemostasis, inflammation, proliferation, and remodeling. Hemostasis includes vasoconstriction, platelet aggregation and degranulation, blood clotting, and fibrin formation. Inflammation represents a cellular cascade beginning with polymorphonuclear leukocytes (PMNs) followed by macrophages and lymphocytes. This stage also provides host defenses against bacterial infection and contributes numerous growth factors, cytokines, and extracellular matrix (ECM) components. The wound macrophage is the crucial inflammatory effector cell that coordinates adult wound repair (Knighton D. R. et al. (1989) *Prog Clin Biol Res* 299:217–226).

The proliferative stage involves multiplication of fibroblasts and endothelial and epithelial cells. The initial proteoglycan-rich fibrin matrix is replaced by collagen. In the final remodeling stage, collagen is cross-linked to form a mature scar. In abnormal wound healing conditions such as keloids, hypertrophic scars, strictures, and intraabdominal adhesions, the final result of wound repair creates a cosmetic or functional problem.

Based on the fact that scar formation and maturation involves a complex interaction of dermal and epidermal cells with the ECM, an artificial ECM model has been used to guide the laying down of a new ECM which results in less scarring (Yannis I. V. et al. (1989) *Proc Natl Acad Sci U.S.A.* 86:933–937). Tension can influence the orientation of organizing collagen, based both on clinical observations and in vitro studies of contracting collagen matrices (Burd D. et al. (1989) *Proc Amer Burns Assoc*, p. 54).

Growth Factors and Wound Healing

Manipulation of the wound healing environment by the application of extrinsic growth factors such as fibroblast growth factor (FGF) and transforming growth factor-β (TGFβ) (Mustoe T. A. et al. (1987) *Science* 237:1333–1336; Seyedin S. M. et al. (1986) *J Biol Chem* 261:5693–5695) can influence the early stages of scar formation. The term "TGFβ" represents a family of 25 kDa dimeric proteins that influence important cell-cell and cell-matrix interactions during embryogenesis, immune responses, and tissue repair. During tissue repair, TGFβ modulates the inflammatory response as a potent chemoattractant for fibroblasts, macrophages, neutrophils and T lymphocytes. TGFβ1 promotes ECM accumulation by increasing the transcription of genes for collagen, fibronectin and glycosaminoglycans and by inhibiting the breakdown of these macromolecules (as described herein). TGFβ can also up-regulate cell surface expression of the integrins that act as receptors for fibronectin, collagen, laminin, and vitronectin thereby influencing cell adhesion and migration. TGFβ enhances the epithelial covering of exposed dermis and increases tensile strength in incisional wounds.

Three mammalian isoforms of TGFβ are known which exhibit an 80% amino acid sequence homology. Until recently, the TGFβ isoforms were thought to be functionally identical, although more recent demonstration of different in vivo effects compared to in vitro activity, and knowledge of the distinction between the three isoforms has prompted further analysis. Immunohistochemical analysis using anti-peptide antibodies specific for each TGFβ isoform has shown distinct expression patterns for each isoform in embryogenesis and carcinogenesis. Distinct promoters for the human TGFβ1, TGFβ2, and TGFβ3 genes provides a mechanism for the observed differential expression in selected tissues. This data coupled with the fact that the three isoforms are 98% conserved across species implies both specific function and complex gene regulation for each TGFβ isoform in vivo, reinforcing the notion that the three isoforms are not simply interchangeable (Seyedin et al., supra). During repair, specific roles for TGFβ isoforms are poorly understood.

Fetal Wound Healing

Human fetal surgery has been successfully performed to treat life-threatening fetal urinary tract obstruction and diaphragmatic hernias (Harrison M. R. et al. (1982) *N Engl J Med* 306:591–593; Harrison M. R. et al. (1987) *J Pediatr Surg* 22:556–558). Following the successful delivery of such babies, it has been observed that scarring or contracture around the decompressing hydronephrostomy tubes was absent. Numerous studies have shown that fetal wounds heal without scarring (Adzick N. S. et al. (1985) *J Ped Surg* 20:315–319; Siebert J. W. et al. (1990) *Plast Reconstr Surg* 85:495–502). Immunohistochemical and biochemical studies (Longaker M. T. et al. (1990) *J Ped Surg* 25:63–69; Adzick et al., supra; Burd D. et al. (1990) *Brit J Plast Surg* 43:571–577) indicate that, as in adults, fetal skin wounds also possess a repair matrix which includes collagen. However in contrast to adult healing, the matrix is rapidly and efficiently organized to appear scarless.

The present invention is intended to exploit knowledge gained from work on fetal wound healing and describe the sequencing of a putative fetal protein factor involved in collagen and matrix organization.

Environmental Differences

Numerous intrinsic and extrinsic differences between the fetus and the adult may drastically influence wound repair. Fetal skin wounds are continually bathed in warm, sterile amniotic fluid rich in growth factors that are crucial to fetal development (Azdick et al., supra). Amniotic fluid is also a rich source for ECM components such as hyaluronan (HA) and fibronectin. Amniotic fluid could modulate fetal skin wound repair simply by supplying HA and fibronectin directly onto fetal skin wounds and by providing growth factors to simulate fetal wound cells to make a unique wound matrix (Azdick et al., supra).

To investigate the influence of the fetal environment on adult tissue repair, full-thickness sheep skin was transplanted onto the backs of 60-day fetal lambs (term=145 days) (Azdick et al., supra), which at that age do not reject allogeneic skin grafts. The adult skin graft was thus bathed in amniotic fluid and perfused by fetal blood; 40 days later (at 100 days gestation), incisional wounds were made on both the adult skin grafts and adjacent fetal skin, and immunohistochemical analysis was performed 7 and 14 days post-wounding. By 14 days the fetal wounds had healed without scarring, while the adult wound collagen pattern was in a typical scar pattern. Thus, neither the amniotic fluid environment nor perfusion by fetal blood prevented scar formation in the wounded adult skin graft. This suggested that the ability of fetal skin to heal without scar formation may be a function of the fetal cells and matrix with or without a fetal environmental influence.

Intrinsic environmental differences include fetal tissue oxygenation, as the fetus depends on transplacental transport from the maternal circulation to meet its oxygen requirements. Because there is a large transplacental oxygen gradient between maternal arterial and umbilical venous blood, fetal arterial blood has a very low $pO_2$ of 20 torr, which is lower than a maskless mountaineer on top of Mt. Everest (Azdick et al., supra). Fetal wound healing in the face of low fetal arterial $pO_2$ seems paradoxical. The answer may lie in an inherent difference between the responsiveness of fetal and adult fibroblasts to differing levels of hypoxemia (Longaker M. T. et al. (1993) *Plast Surg Res Council*).

Some of the properties of fetal skin wound healing may reflect the development of fetal skin. However, healing of fetal bone is also different from adult bone. Virtually no callus formation is present at any time during the healing of fetal lamb bone, and healed fracture sites are indistinguishable radiologically and histologically from uninjured bone. In addition, large bony defects in the fetus, which would be unhealable in infants or adults do close. Not all fetal tissues appear to share the remarkable regenerative qualities of fetal skin and bone. In in utero repair of previously surgically created fetal diaphragmatic hernias, the fetal intestine was always densely adherent to the diaphragmatic defect, but no scar was evident on the previously made thoracic skin incision. Clinical experience with human fetal surgery has shown extensive intraabdominal adhesions following fetal diaphragmatic hernia repair. Thus, fetal mesothelial wounds may heal differently from fetal skin wounds. In addition, amniotic fluid exposure may play an important role in the scarless healing of fetal skin wounds, but its effect on the healing of fetal mesothelial wounds has not been demonstrated.

Fetal Inflammation

Another intrinsic difference between the fetus and adult lies in the inflammatory and immune systems. Histologically, there are few, if any, PMNs in fetal wounds, and there may be a defect in immature PMN chemotactic ability. Fetal lamb wounds lack the typical inflammatory response seen in adult sheep (Longaker M. T. et al., 1990, supra). Because of the prominent role that inflammation plays in adult tissue repair, the minimal fetal inflammatory response to injury may play a pivotal role in the unique fetal repair process. Introduction of adult acute inflammatory cells into the fetus attracts fetal PMNs to the wound site, but an adult fibrotic type of healing response does not follow. These intriguing findings raise questions regarding what attracts fetal fibroblasts into the wounds, how this differs between fetus and adult, and whether characteristic inflammatory mediators of adult wound healing are absent in fetal wounds.

The wound macrophage is the crucial inflammatory cell orchestrating adult wound healing (Knighton et al., supra). Neutrophils can be eliminated from wound repair without a defect in granulation tissue but macrophages cannot. Macrophages are essential regulatory cells that coordinate matrix debridement and turnover, and secrete mediators of inflammation, angiogenesis, and cell growth (Knighton et al., supra). Fetal rabbit wounds, though lacking in PMNs, have an abundance of macrophages (Adzick N. S. et al., 1985, supra). In addition to regulation through growth factor expression, wound macrophages are involved in matrix turnover through proteinase expression. Their secretion of metalloproteinases (e.g., collagenase) and proteinase inhibitors coordinates the degradation and remodeling of the wound ECM. The observation that fetal lamb incisional wounds appear histologically indistinguishable from unwounded skin within two weeks suggests that fetal wound matrix turnover and repair are rapid and efficient (Longaker M. T. et al., 1990, supra).

Fetal Growth Factors

In the fetus, wounds made before the mid-third trimester heal with a collagen repair matrix so organized as to appear scarless, but as in adults, growth factors can modulate the healing wound.

Addition of TGFβ or PDGF converted a fetal injury response to an adult-like injury response (Krummel T. M. et al. (1988) *J Ped Surg* 23:647–652). Administration of anti-TGFβ antibodies blocked the increased fibrosis in a wound treated with TGFβ1 (Shah M et al. (1992) *Lancet* 339:213–214). These results further implicate TGFβ in scar formation. In fetal mouse lip wounds that normally heal without scarring, the presence of TGFβ1 or β2 isoforms could not be detected immunohistochemically with neutralizing antibodies (Whitby D. J. et al. (1991) *Dev Biol* 147:207–215). This is in stark contrast to neonatal and adult lip wounds which did immunostain for both isoforms. However, it has been shown that fetal wound fluid is abundant in TGFβ even during the period of scarless healing, although, interestingly, there is a change in the relative concentrations of isoforms as gestation progresses (Roberts A. B. et al. (1993) *J Cell Biol Supplement* 17E).

Thus, the presence of growth factors in vivo in healing wounds demonstrated by immunohistochemical staining, neutralizing antibody techniques, and direct assay of wound chamber fluid, supports the concept that growth factors are important in modulating wound healing in the fetus as in the adult.

Hyaluronan

Hyaluronan (HA), formerly called hyaluronic acid or hyaluronate (Balaz E. A. et al. (1986) *Biochem J.* 233:903), is found in high concentration in ECM wherever tissue repair occurs after injury (Toole, B. P., In: Hay E. D., ed., *CELL BIOLOGY OF THE EXTRACELLULARMATRIX.* New York: Plenum Press; pp. 259–294, 1982). HA is a glycosaminoglycan (GAG) laid down early in the matrix of both fetal and adult wounds. Sustained deposition of HA is unique to fetal skin, where injury repair occurs with less scarring and more rapidly than adult injury repair. HA appears to provide an extracellular environment conducive to cell mobility and proliferation that may provide the matrix signal responsible for orchestrating healing by regeneration rather than by scarring in the fetus. The fetal wound matrix is rich in HA (Krummel T. M. et al., 1987, supra; De Palma R. L. et al. (1987) *Surg Forum* 38:626–628; De Palma R. L. et al. (1989) *Matrix* 9:224–231)). By implanting PVA sponges into 24 day fetal rabbits or into adult rabbits, it was found that the GAG content of fetal sponges was significantly greater on day 2 through 6 when compared to adult sponges, and had 10 times the amount of GAG found in unwounded fetal skin. The major GAG component was HA, as determined by cellulose acetate electrophoresis followed by alcian blue staining (DePalma et al., 1989, supra; Longaker M. T. et al. (1989) *Ann Surg* 210:667–672).

A role for HA in the scarless healing in the fetus is supported by studies in which topical application of HA tissue extracts modulated post-natal healing, and, for example, enhanced wound healing in rat tympanic membrane perforations (Hellstrom S. et al. (1987) *Acta Otolaryngol* 442 (*Suppl*):7–24). HA facilitated wound healing in diabetic rats by promoting epithelial migration and differentiation (Abatangelo G. et al. (1983) *J Surg Res* 35:410–416). HA-treated wounds developed a greater early wound breaking strength compared to untreated controls, reportedly due to an early accumulation of oriented collagen fibers (Radelli E. et al. (1982) *Int'l. Symp. Cutaneous Development, Aging and Repair,* University of Padova, p. 42). However, attributing the wound healing effects exclusively to HA is difficult. It is important to remember that tissue-extracted HA, for example from rooster comb or human umbilical cord, is always "contaminated" with one or more proteins, including collagen (Swann D. A. et al. (1975) *Ann Rheum Dis* 34 (*Suppl*):98–100).

The present inventors and their colleagues identified a heterogenous group of HA-protein complexes in normal skin and post-burn scar and confirmed the association of HA and collagen. Further, they found that HA extracted from normal skin, normal scar, and hypertrophic scar demonstrated qualitative and quantitative variation in other non-collagen associated proteins despite identical extraction and purification techniques (Burd D. A. R. et al. (1989) *Matrix* 9:322–327).

SUMMARY OF THE INVENTION

The present inventors have conceived of the use of hyaluronan associated proteins (HA-AP), in particular a protein appearing as a 62 kDa HA-AP, calreticulin, for promoting the scarless healing of wounds, such as surgical wounds or wounds incurred in accidental trauma.

The present invention is therefore directed to a method of promoting the more rapid healing of a wound with diminished scar formation in a subject, comprising administering to the subject in need of such treatment an amount of a hyaluronan-associated protein, or a functional derivative thereof, effective in promoting scarless healing of wounds.

Also provided is a method for modulating the expression of TGFβ isoforms in the healing tissue of a wound in a subject, such that TGFβ3 expression is enhanced and TGFβ1 expression and TGFβ2 expression are inhibited, which method comprises administering to the subject an amount of a hyaluronan-associated protein, or a functional derivative thereof, effective in enhancing TGFβ3 and inhibiting TGFβ1 and TGFβ2.

In the above methods, the hyaluronan-associated protein preferably has an apparent molecular weight of about 62 kDa upon SDS-PAGE under reducing conditions. Most preferably, the protein is calreticulin.

The above methods may further comprise administering to the subject, in combination with the hyaluronan-associated protein or functional derivative, an effective amount of at least one other agent useful in promoting the healing of a wound. A preferred agent is an anti-bacterial agent, an anti-viral agent, an anti-fungal agent, a local anesthetic, an analgesic, and a growth factor. Preferred growth factors include transforming growth factor-α, transforming growth factor-β, fibroblast growth factor-α, fibroblast growth factor-β, epidermal growth factor, platelet-derived growth factor, endothelial cell-derived growth factor, insulin-like growth factors, and granulocyte colony-stimulating factor.

In the above methods, the hyaluronan-associated protein, or calreticulin, or functional derivative, may be administered in a form associated with a solid or semisolid phase support material.

The above methods are preferably used for treating a wound caused by physical or surgical trauma.

The present invention is also directed to a pharmaceutical composition useful in the promotion of scarless wound healing, comprising:

(a) an amount of a hyaluronan-associated protein or a functional derivative thereof effective for treating wounds; and (b) a pharmaceutically acceptable carrier.

Preferably, the protein has an apparent molecular weight of about 62 kDa on SDS PAGE. Most preferably, the protein is calreticulin.

The above pharmaceutical composition may further comprise (c) at least one other agent useful in promoting the healing of a wound.

Preferred agents include an anti-bacterial agent, an anti-viral agent, an anti-fungal agent, a local anesthetic, an analgesic and a growth factor.

BRIEF DESCRIPTION OF THE DRAWINGS

FIG. 1 shows the results of immunostaining for TGFβ isoforms (TGFβ1, TGFβ1 and TGFβ3) using highly isoform-specific murine antibodies in adult sheep incisional wounds.

FIG. 2 shows the results of immunostaining for TGFβ isoforms (TGFβ1, TGFβ1 and TGFβ3) using highly isoform-specific murine antibodies in adult sheep excisional wounds.

DESCRIPTION OF THE PREFERRED EMBODIMENTS

Figure 3:
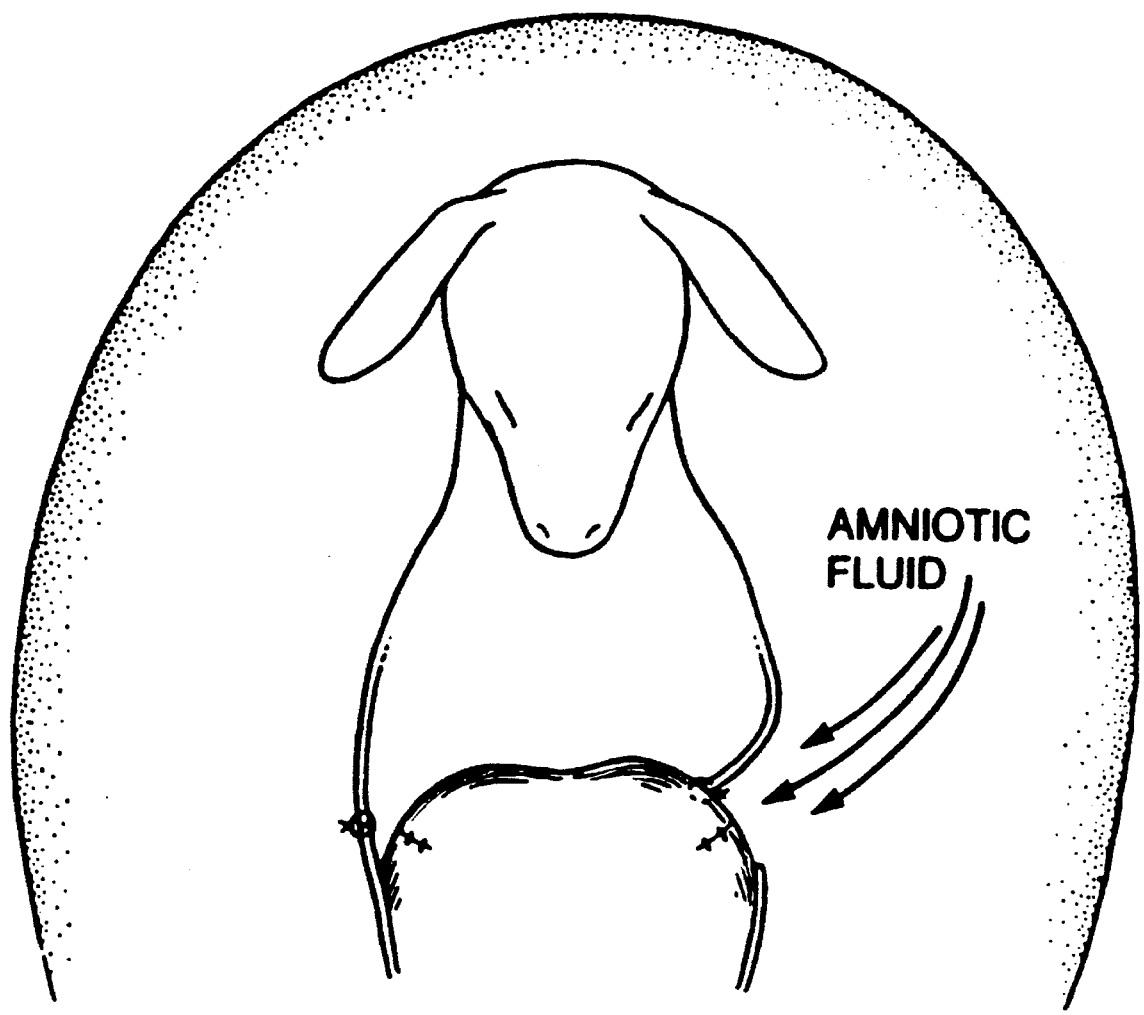
FIG. 3 shows a right thoracotomy which was closed to exclude the right diaphragmatic wound from amniotic fluid, and the Eloesser thoracoplasty flap which permits the left diaphragmatic wound to be exposed to amniotic fluid.
Figure 4:
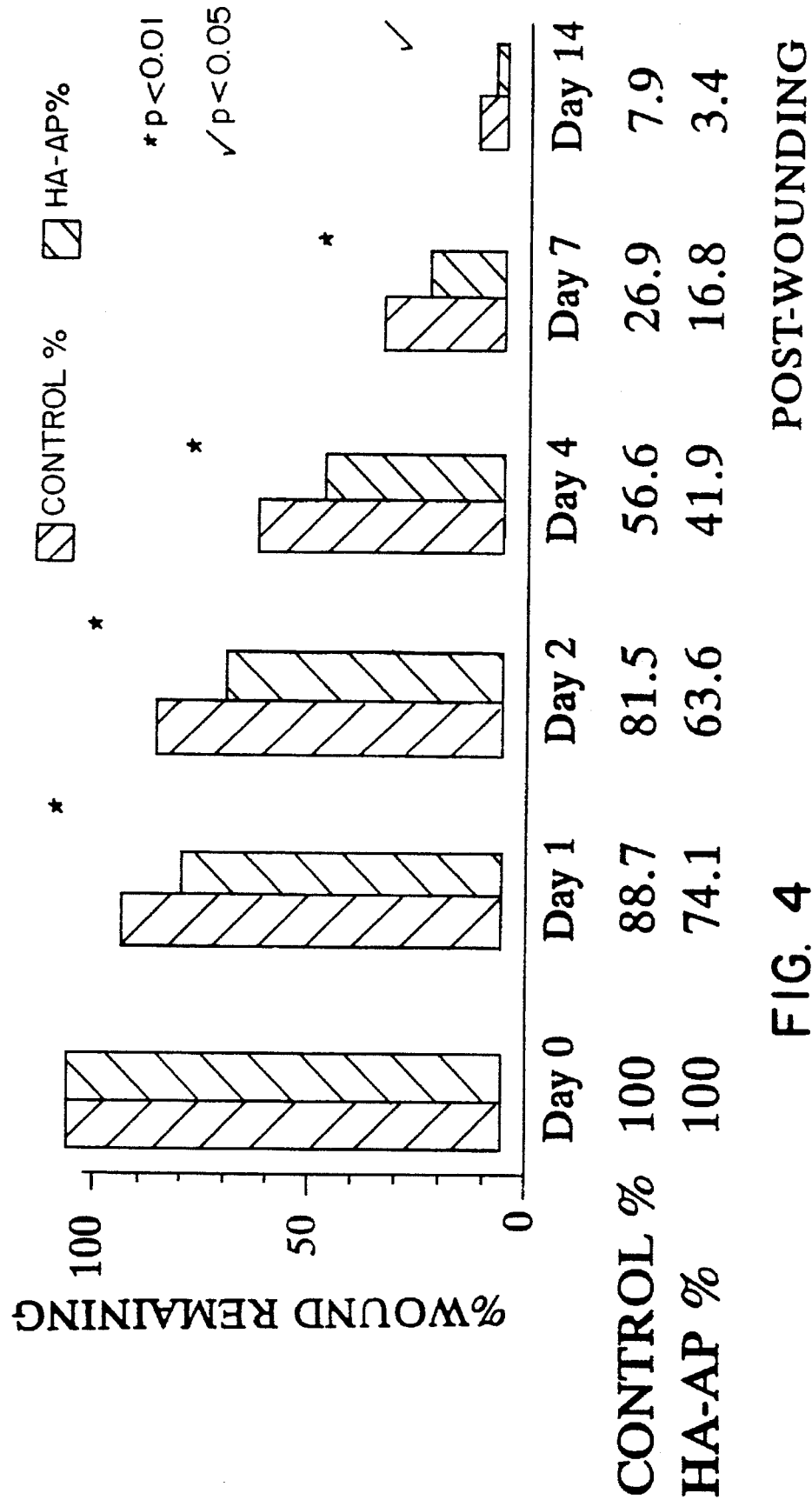
FIG. 4 shows the wound area remaining in adult rat excisional wounds treated with hyaluronan associated protein dissolved in a petrolatum/lanolin vehicle up to 14 days post-wounding compared to control wounds treated with vehicle alone.

The present inventors have discovered that hyaluronan in combination with its associated proteins (HA-AP), as isolated from tissues, act to promote more rapid and relatively scarless wound healing. HA-AP applied topically to a wound promotes both the rate of healing as well as the amount of scarless healing. As used herein, the term "promote wound healing" is intended to include both the rate of healing as well as the diminution of scar formation. The term "scarless" as used herein refers both to healing with no scar tissue as well as healing with diminished scar formation.

Also noted by the present inventors was that HA-AP regulates the expression of three isoforms of transforming growth factor-β (TGFβ). Thus, treatment with HA-AP enhanced expression of TGFβ3 while inhibiting expression of the fibrogenic isoforms TGFβ1 and TGFβ2, as detected with isoform specific antibodies.

Importantly, the present inventors have discovered that the 62 kDa protein associated with HA which is important for scarless wound healing is calreticulin, a protein which has been previously described and cloned (Fliegel, L. et al. (1989) *J. Biol. Chem.* 264:21522–21528; Baksh, S. et al., (1991) *J. Biol. Chem.* 266:21458–21465; Rokeach, L. A. et al., (1991) *Prot. Engineering* 4:981–987; Baksh, S. et al. (1992) *Prot. Express. Purific.* 3:322–331; Michalak, M. et al., (1992) *Biochem. J.* 285:681–692). Calreticulin was originally identified as an intra-endoplasmic reticulum low affinity, high capacity calcium-binding protein found in non-skeletal muscle cells which shows remarkable homology between mammalian species.

Thus the present invention is directed to methods for promoting the scarless healing of a wound comprising administering an effective amount of HA-AP, more preferably, a 62 kDa protein of HA-AP, most preferably, calreticulin. In these methods, functional derivatives of the above protein or proteins may also be administered. Also provided are pharmaceutical compositions comprising HA-AP, more preferably a 62 kDa protein of HA-AP, most preferably, calreticulin, or a functional derivative thereof.

Proteins, Peptides and Their Functional Derivatives

The present invention is directed to compositions and methods for promoting scarless healing of a wound using HA-AP as well as calreticulin. Also included are peptides or other functional derivatives of the HA-associated protein or of calreticulin which have the functional activity of promoting accelerated and scarless wound healing.

It will be understood that the protein useful in the methods and compositions of the present invention can be biochemically purified from a cell or tissue source. For preparation of naturally occurring HA-AP or calreticulin, any of a number of tissues of adult or of fetal origin can be used. Methods for purifying HA-AP are well-known in the art. See, for example, DePalma et al., 1989, supra; Longaker et al. (1989) supra; (Swann et al. (1975) supra; Burd et al. (1989) *Matrix* 9:322–327, which references are hereby incorporated by reference in their entirety).

Alternatively, because the gene encoding calreticulin is known (Fliegel et al., supra; Baksh et al., (1991) supra; Rokeach et al., supra; Baksh et al. (1992) supra; Michalak et al., supra) and can be isolated or synthesized, the polypeptide can be synthesized substantially free of other proteins or glycoproteins of mammalian origin in a prokaryotic organism or in a non-mammalian eukaryotic organism, if desired. Alternatively, methods are well known for the synthesis of polypeptides of desired sequence on solid phase supports and their subsequent separation from the support.

Preparation of HA-AP and Calreticulin

Tissue Extraction

Frozen fetal sheep skin is thawed at room temperature and multiple specimens from time dated ewes are pooled and finely minced into 0.5 cm pieces using scissors. The intracellular and extracellular components of the skin matrix are extracted using a solution of 4M guanidine-HCl containing proteinase inhibitors. Four ml of buffer are used per gram of wet fetal skin. The mixture is gently stirred for 72 hours at 4° C. Larger pieces of skin are separated from the extract using cheesecloth. To maximize yield, the extraction procedure may be repeated. The extract is centrifuged for 30 min at 36,000 rpm using a 60Ti Beckman rotor. The supernatant is dialyzed against distilled water until free of guanidine-HCl when tested with 1% silver nitrate. The extract is then resuspended in a solution of 7M urea and 0.15M Tris (Buffer N) titrated to a pH of 7.5 using HCl. The resuspended extract is again centrifuged as above until all solid and undissolved particles are removed.

Anion Exchange Chromatography

Anion exchange chromatography using diethylaminoethyl cellulose (DEAE 52), a technique well-known in the art, is used to fractionate the extract. The extract is loaded on a DEAE column and washed with 4 time the column volume with Buffer N. An increasing gradient of from 0.2M to 1.0M NaCl in buffer N is used to separate the extract into fractions of unbound protein, collagen, hyaluronic acid and sulfated glycosaminoglycans. These fractions are analyzed for uronic acid content using the Carbazole reaction. Absorbance at 530 nm are used to detect uronic acid concentration. Absorbances at 280 nm are used to measure protein. Based on the elution profile, samples are pooled and dialyzed against water until free of urea. Samples are lyophilized. Impure or mixed samples containing sulfated and nonsulfated glycosaminoglycans are further purified using smaller (15–30 ml) anion exchange column as above.

Alcohol Precipitation

Alcohol precipitation with ethanol is used to partially purify samples which cannot be purified by anion exchange chromatography. The samples are dissolved in 4M guanidine HCl solution. Ethyl alcohol is added to achieve a 25% alcohol guanidine mixture and the solution centrifuged at 36,000 rpm for 45 minutes. The supernatant is preserved an resuspended to a 50% ethanol concentration. The pellet is dissolved in 1M NaCl, dialyzed against water, and lyophilized. This procedure is then repeated with increasing ethanol concentrations of 50% and 75%.

Cellulose Acetate Electrophoresis

Purity of the samples is confirmed by cellulose acetate electrophoresis. Dry sample are resuspended in water, and 1–2 µl aliquots are placed on cellulose acetate plates. Standard samples containing sulfated and non-sulfated glycosaminoglycans are place on either side of the test samples. Cellulose acetate plates are stained with 1% alcian blue stain and destained with 5% acetic acid. This method detects polysaccharides of MW >7.2 kDa and is sensitive to 0.1 µg of glycosaminoglycans.

Purified samples of hyaluronic acid are suspended in buffer containing 0.15M NaCl and 0.1M Sodium acetate titrated to pH 5. The samples are treated with hyaluronidase and incubated at 60° C. for 4 hours. Disappearance of the characteristic hyaluronic acid bands on cellulose acetate electrophoresis confirms the purity of the samples.

Polyacrylamide Gel Electrophoresis (PAGE)

PAGE is performed sing a 5%–20% gradient resolving gels and a 3.5% stacking gel to demonstrate the presence of the HA-APs. The preferred technique is a modification of the method of D. A. Swann et al. (1983) *J. Biol. Chem.* 258:2683–2688. Highly purified dried samples of fetal HA and its associated protein are dissolved in reducing buffer to disrupt interchain disulfide bonds. The samples are boiled to break protein aggregates. Successively increasing concentrations of sample are applied to the gels along with high and low MW standards used as references until protein banding is demonstrated. Gels are stained with 1% coomassie blue and destained with methanol-acetic acid in distilled water.

Hyaluronic Acid Content of Samples

The uronic acid content of samples is quantitated using the carbazole reaction. Standard samples of HA derived from rooster comb are analyzed. Absorbance is measured at 530 nm.

Protein concentration is measured using the Lowry method, with BSA as standard.

Microanalysis of SDS-PAGE Electroblotted Protein

The current availability of chemically stable membranes provides the means for direct sequencing of peptides after being electroblotted in microgram quantities, for example from a SDS gel. Aebersold et al., developed such a PAGE electroblotting method to isolate microgram quantities of protein for amino acid sequence analysis. This system also offers a means of purifying the protein to be sequenced by differential mobilities based on the protein MW. In the present methods, extracted fetal HA-AP, for example from 90 days of gestation is electroblotted to nylon PVDF (Immobilon; Millipore) membranes. The proteins are transferred for 1.5 hours and stained for 30 seconds with 0.1% fast Green, 10% glacial acetic acid, and 25% methanol, and destained in 5% acetic acid for 1 minute, and washed profusely with distilled water for 20 minutes. The membranes are then encased in plastic wrap and the sequence determinations performed. This process is repeated for each band on SDS-PAGE. Available protein and DNA databases are used to identify the sequenced protein. If the protein is blocked at its N-terminus, internal sequence analysis is performed by a technique based on CNBr cleavage and ortho-phthaldehyde blocking of the N-terminus of fragments not containing proline. The biological activity and dose response of proteins purified, identified and sequenced in this way will be tested as described below.

The above method was used to identify the 62 kDa HA-AP as having identical amino acid sequence with calreticulin.

In a further embodiment, the invention provides "functional derivatives" of a HA-AP, particularly, of calreticulin. By "functional derivative" is meant a "fragment," "variant," "analog," or "chemical derivative" of calreticulin. A functional derivative retains at least a portion of the function of calreticulin, such as the activity of promoting scarless wound healing, upregulating TGFβ3 expression in skin, or binding to a specific anti-calreticulin antibody, which permits its utility in accordance with the present invention.

A "fragment" of calreticulin refers to any subset of the molecule, that is, a shorter peptide.

A "variant" of calreticulin refers to a molecule substantially similar to either the entire protein or a fragment thereof. Variant peptides may be conveniently prepared by direct chemical synthesis of the variant peptide, using methods well-known in the art.

Alternatively, amino acid sequence variants of the protein or peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired functional activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the calreticulin protein or a peptide fragment thereof, thereby producing DNA encoding the variant, and thereafter expressing the DNA in recombinant cell culture (see below). The variants typically exhibit the same qualitative biological activity as the nonvariant peptide.

A preferred group of variants of calreticulin are those in which at least one amino acid residue in the protein or in a peptide fragment thereof, and preferably, only one, has been removed and a different residue inserted in its place. For a detailed description of protein chemistry and structure, see Schulz, G. E. et al., *PRINCIPLES OF PROTEIN STRUCTURE,* Springer-Verlag, New York, 1978, and Creighton, T. E., *PROTEINS: STRUCTURE AND MOLECULAR PROPERTIES,* W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1-2 of Schulz et al. (supra) and FIGS. 3–9 of Creighton (supra). Base on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and 5. Large aromatic residues: Phe, Tyr, Trp.

The three amino acid residues in parentheses above have special roles in protein architecture. Gly is the only residue lacking any side chain and thus imparts flexibility to the chain. Pro, because of its unusual geometry, tightly constrains the chain. Cys can participate in disulfide bond formation which is important in protein folding. Note the Schulz et al. would merge Groups 1 and 2, above. Note also that Tyr, because of its hydrogen bonding potential, has some kinship with Ser, Thr, etc.

Substantial changes in functional or immunological properties are made by selecting substitutions that are less conservative, such as between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro by another amino acid or deletion or insertion of gly or pro; (b) substitution of a hydrophilic residue, such as ser or thr, for (or by) a hydrophobic residue, such as leu, ile, phe, val or ala; (c) substitution of a cys residue for (or by) any other residue; (d) substitution of a residue having an electropositive side chain, such as lys, arg or his, for (or by) a residue having an electronegative charge, such as glu or asp; or (e) substitution of a residue having a bulky side chain, such as phe, for (or by) a residue not having such a side chain, such as gly.

Preferred deletions and insertions, and substitutions, according to the present invention, are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays which are described in more detail below. For example, a change in the immunological character of the protein peptide molecule, such as binding to a given antibody, is measured by a competitive type immunoassay. Biological activity is screened in an appropriate bioassay, as described below.

Modifications of such peptide properties as redox or thermal stability, hydrophobicity, susceptibility to proteolytic degradation or the tendency to aggregate with carriers or into multimers are assayed by methods well known to the ordinarily skilled artisan.

An "analog" of calreticulin refers to a non-natural molecule substantially similar to either the entire molecule or a fragment thereof.

A "chemical derivative" of calreticulin contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Additionally, modified amino acids or chemical derivatives of amino acids of calreticulin or fragments thereof, according to the present invention may be provided, which polypeptides contain additional chemical moieties or modified amino acids not normally a part of the protein. Covalent modifications of the peptide are thus included within the scope of the present invention. The following examples of chemical derivatives are provided by way of illustration and not by way of limitation.

Aromatic amino acids may be replaced with D- or L-naphthylalanine, D- or L-phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanine, and D- or L-alkylalanine where alkyl may be substituted or unsubstituted methyl, ethyl, propyl, hexyl, butyl, pentyl, isopropyl, isobutyl, sec-isotyl, isopentyl, non-acidic amino acids, of chain lengths of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (for example, —$SO_3H$) threonine, serine, tyrosine.

Other substitutions may include unnatural hydroxylated amino acids may made by combining "alkyl" with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (for example, containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage the polypeptides can be replaced by a ketomethylene moiety, for example, (—C(=O)—$CH_2$—) for (—(C=O)—NH—). Such derivatives are expected to have the property of increased stability to degradation by enzymes, and therefore possess advantages for the formulation of compounds which may have increased in vivo half lives, as administered by various routes as described herein.

In addition, any amino acid representing a component of the peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D-amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by various routes.

Additional amino acid modifications in calreticulin or in a peptide thereof may include the following.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides, which reverses the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

The specific modification of tyrosyl residues has been studied extensively with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histidine side chains (Creighton, supra), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Production of Calreticulin and Fusion Proteins that Promote Scarless Wound Healing Calreticulin may be purified from a tissue source using conventional biochemical techniques, or produced recombinantly in either prokaryotic or eukaryotic cells using methods well-known in the art (Sambrook, J. et al., *MOLECULAR CLONING: A LABORATORY MANUAL*, 2nd Edition, Cold Spring Harbor Press, Cold Spring Harbor, N.Y., 1989, which reference is hereby incorporated by reference in its entirety). Various references describing the cloning and expression of calreticulin have been noted above.

Fusion proteins representing different polypeptide regions in calreticulin may be used to identify regions of the protein that have the desired functional activity (binding, stimulating wound healing, etc.). When combined with the polymerase chain reaction (PCR) method, it is possible and expedient to express in bacteria nearly any selected region of the protein.

To facilitate unidirectional subcloning of the PCR products, sense and antisense oligonucleotides have been designed to include BamH1 recognition sequences at the 5' end and EcoR1 recognition sequences at the 3' end, respectively; appropriately digested PCR products are then be ligated directly into a vector (such as the pGEX-2T vector). Use of this methodology allows construction of vectors and purification of several fusion proteins in less than one month.

The pGEX vector is preferred because the glutathione-S-transferase (GST) fusion proteins can be purified rapidly by binding to glutathione-agarose beads. In addition, because cDNAs are cloned into pGEX-2T, the portion of the fusion protein representing the GST can be cleaved with thrombin and the engineered polypeptide can generally be recovered free of the GST protein which can be removed using glutathione-agarose beads (Ausubel, F. M., et al., 1990, *CURRENT PROTOCOLS IN MOLECULAR BIOLOGY*, John Wiley & Sons, New York.

Calreticulin, a peptide thereof, or a fusion protein thereof may also be expressed in insect cells using baculovirus expression system. Production of calreticulin or functional derivatives thereof, including fusion proteins, in insects can be achieved, for example, by infecting the insect host with a baculovirus engineered to express calreticulin by methods known to those of skill. Thus, in one embodiment, sequences encoding calreticulin may be operably linked to the regulatory regions of the viral polyhedrin protein (Jasny, 1987, *Science* 238:1653). Infected with the recombinant baculovirus, cultured insect cells, or the live insects themselves, can produce the calreticulin or functional derivative protein in amounts as great as 20 to 50% of total protein production. When live insects are to be used, caterpillars are presently preferred hosts for large scale production according to the invention.

Fragments of calreticulin are purified by conventional affinity chromatography using antibodies, preferably monoclonal antibodies (mAbs), that recognize the appropriate regions of calreticulin. The mAbs specific for the most highly conserved regions in calreticulin can be used to purify calreticulin protein from mixtures.

Wound Healing Assays

To characterize functions of HA-AP, of calreticulin, and of different regions in calreticulin, any of a number of assays may be used. These assays may be used routinely to analyze the biological functions of calreticulin or other HA-AP of the present invention.

Fibroblast Assays

A. Fibroblast Proliferation

Normal human dermal fibroblast cultures are maintained in a humidified 5% $CO_2$ incubator at 37° C. Preferred medium is Dulbecco's modified Eagle's medium (DMEM) supplemented with 10% fetal bovine serum and antibiotics. The presence of fetal bovine serum at this concentration has no effect on HA-AP activity. Cultures are established in 35 mm dishes with $10^5$ cells/dish in 2 ml medium. The test preparation, for example, HA-AP or calreticulin, is added at the time of plating or 24 hours later. Cultures are pulsed with $^3$H-thymidine for 24 hours beginning at 24 or 48 hours of culture. Cells are harvested at 48 or 72 hours using trypsin, counted and isotope incorporation is measured by liquid scintillation counting. DNA content in the culture is also measured. Since fibroblasts are the cells responsible for matrix accumulation in scarring, it is expected that the agents active in promoting scarless wound healing would inhibit fibroblast proliferation.

B. Fibroblast Motility

Fibroblast-populated collagen lattice (FPCL (Bell, E. et al., (1979) *Proc. Natl. Acad. Sci. U.S.A.* 76:1274) is composed of soluble collagen, cultured fibroblasts and serum-enriched culture medium, which are rapidly mixed. The collagen polymerizes, entrapping cells within it. Over time, the cells within the lattice cause a reorganization of the matrix, with condensation and local alignment of collagen fibrils. The overall effect is the shrinkage of the lattice, referred to as "lattice contraction. Acid soluble rat tail tendon and pepsin solubilized human leiomyoma collagens are isolated by salt precipitation. After extensive dialysis, the collagen solutions are frozen, lyophilized and resuspended in sterile 1 mM HCl at 5 mg/ml and stored at 4° C. Standard lattice preparation involves gentle vortex mixing of 1 ml of culture medium, 0,5 ml of cells and 0.5 m of collagen solution, and rapid pouring of the mixture into 35 mm dishes which are incubated at 37° C. HA-AP or calreticulin preparations are added either (a) at the time of lattice formation, (b) after polymerization, or (c) at 24 hrs. The lattices are measured using computerized morphometrics to give an area of the lattice for each 12 hours, and the rate of contraction is recorded. The rate of contraction is determined for the varying doses of test agents applied. It is expected that the wound healing promoting compounds of the present invention increase contraction.

C. Fibroblast Metabolism

Comprehensive analysis of collagen metabolism is performed with and without the various test compounds, using double labeling techniques (Bateman, J. F. et al., (1988) *Anal. Biochem.* 168:171–175). Confluent fibroblast monolayer cultures are incubated with a mixture of D-[4-$^{14}$C]-proline and L-[4-$^3$H-proline in medium with and without fetal bovine serum. Following incubation, the cell layer and medium fractions are treated separately. Collagens in the medium are precipitated with ammonium sulfate and resuspended in 50 mM Tris-HCl pH 7.5, containing 0.15M NaCl and proteinase inhibitors. Procollagen is precipitated by addition of ethanol and converted to α-chains by limited pepsin digestion. The cell fraction is sonicated and centrifuged. DNA analysis is performed on half of the solution and collagen precipitated from the other half. Again, procollagen is isolated and α-chains produced by limited pepsin digestion.

Collagen production and secretion, and proline hydroxylation is analyzed by the incorporation of $^{14}$C-protein into bacterial collagenase-digestible protein and assessing changes in the $^3$H:$^{14}$C proline ratios. The production and secretion of individual types of collagen is assessed by incorporation of $^{14}$C proline into individual a-chains, separated by gel electrophoresis, and quantified by liquid scintillation counting of excised portions of the gel. Collagen production/secretion experiments are also done by using one radiolabeled precursor in culture and determining the hydroxyproline contents.

Re-epithelization Assays in a Dermal Explant Model

A. Epidermal Cell Proliferation

Dermal sheets from paravertebral areas of domestic pig skin are obtained under aseptic conditions with a Pagett's dermatome at a setting of 0.5 mm after removing a 0.5 mm thick split thickness graft containing the epidermis. Dermal strips are cut into 1 cm2 segments and transferred onto stile dressing sponges in multiwell Petri dishes to raise the explant to the air liquid interface. Orientation of the dermis is maintained. Explants are kept in a 10%CO2 environment with 95% humidity in serum free DME supplemented by 10 ng/ml hydrocortisone without antibiotics.

The test compound is suspended in sterile PBS at various concentrations and applied to the explant (75 μ/cm2) at day o only or at the time of medium exchanges every 4 days. Explant cultures are harvested after 4, 8 or 12 days and fixed in 10% formalin. Re-epithelialized areas around hair follicles are visualized by staining with 1% rhodamine solution for a few seconds and washing in formalin. Resurfaced areas are photographed at a magnification of 10× and their size determined by computerized morphometric analysis. The ration of area of re-epithelialization to the cross sectional area of the hair follicle is determined.

Full Thickness in vivo Wound Healing Models

Full thickness paired 1 cm incisional and paired 1 cm2 excisional wounds are made with a sterile scalpel on the dorsa of male Sprague-Dawley rats. The test compound, suspended in PBS, is injected into the incisional wound margins or dissolved in a vehicle such as 70:30 lanolin petrolatum with proteinase inhibitor and applied topically to the excisional wounds. The test compound is applied daily to an incisional and excisional wound on each animal. The paired wound is treated daily with the corresponding control (PBS alone or lanolin-petrolatum vehicle). Animals are housed individually and their wounds are covered daily. Treatment is randomized to right or left side independently for incisional and excisional wounds. Wound closure is determined by tracing the excisional wounds on acetate sheets and measuring their areas using computer assisted planimetry. Animals are sacrificed at specified intervals after wounding and the tissue fixed overnight i 10% buffered formalin and embedded in paraffin. Hematoxylin and eosin staining of section is used to count inflammatory cells at wound margins per high power filed. Masson's trichrome stained slides are graded for collagen organization based on the thickness and orientation of collagen fibers and the extent of scar present. Immunohistochemistry is performed using various antibodies as described herein, including TGFβ isoform-specific antibodies, anti-fibronectin antibodies and antibodies to collagen types I and III. After relative effects of a given protein, peptide, etc. on wound healing is determined, dose response relationships are obtained using the above model.

In the above assays, wounds treated with a sample containing a HA-AP having activity for promoting healing, or having calreticulin, heal more quickly. Specificity may be tested by including an anti-calreticulin antibody or an antibody against another HA-AP in the treatment mixture. If an anti-calreticulin antibody inhibits the bioactivity of the test sample, the activity can be attributed to calreticulin.

Therapeutic Applications of Hyaluronan-Associated Proteins and Calreticulin

The preferred animal subject of the present invention is a mammal. By the term "mammal" is meant an individual belonging to the class Mammalia. The invention is particularly useful in the treatment of human subjects.

The present invention provides for methods of treatment of wounds, which methods comprise administering to a subject in need of such treatment an effective amount of an HA-AP, preferably a 62 kDa protein of HA-AP, most preferably, calreticulin, or a functional derivative thereof, that promote the scarless healing of a wound.

The disorders that may be treated according to this invention include, but are not limited to surgical wounds, wounds incurred in accidents, or wounds associated with any of a number of diseases including cancer and infectious disease.

Effective doses of calreticulin for therapeutic uses discussed above may be determined using methods known to one skilled in the art. Effective doses may be determined, preferably in vitro, in order to identify the optimal dose range using various of the methods described herein. In one embodiment, an aqueous solution of a calreticulin protein or peptide is administered by intravenous injection. Each dose may range from about 0.001 µg/kg body weight to about 100 mg/kg body weight, or more preferably, from about 0.1 µg/kg to 10 mg/kg body weight. The dosing schedule may vary from once a week to daily depending on a number of clinical factors, including the type of wound, its severity, and the subject's sensitivity to the protein. Nonlimiting examples of dosing schedules are 3 µg/kg administered twice a week, three times a week or daily; a dose of 7 µg/kg twice a week, three times a week or daily; a dose of 10 µg/kg twice a week, three times a week or daily; or a dose of 30 µg/kg twice a week, three times a week or daily. In the case of a more severe wound, it may be preferable to administer doses such as those described above by alternate routes, including intravenously or intrathecally. Continuous infusion may also be appropriate.

Calreticulin or a functional derivative may also be administered in combination with an effective amount of at least one other agent that is, itself, capable of promoting the healing of wounds or treating accompanying symptoms. Such agents include growth factors, anti-infectives, including anti-bacterial, anti-viral and anti-fungal agents, local anesthetics, and analgesics, or a combination thereof.

The calreticulin may be administered in any pharmaceutically acceptable carrier. The administration route may be any mode of administration known in the art, including but not limited to intravenously, intrathecally, subcutaneously, or intracranially by injection into involved tissue, intraarterially, orally, or via an implanted device.

The present invention also provides pharmaceutical compositions comprising an amount of a HA-AP, preferably a 62 kDa protein of an HA-AP, most preferably, calreticulin, or a functional derivative thereof effective to promote the scarless healing of a wound, in a pharmaceutically acceptable carrier.

Also provided is a pharmaceutical composition comprising an effective amount of calreticulin together with one or more additional agents in a pharmaceutically acceptable carrier. Such additional agents include agents which are known to promote wound healing or to treat problems or symptoms associated with wounds. Examples of such agents include disinfectants such as antibacterial agents or antiviral agents, anti-fungal agents, anti-inflammatory agents, agents which induce relief from pain or itching, and the like. Also included are growth factors which promote wound healing, including, but not limited to, transforming growth factor-$\alpha$, transforming growth factor-$\beta$, fibroblast growth factor-$\alpha$, fibroblast growth factor-$\beta$, epidermal growth factor, platelet-derived growth factor, endothelial cell-derived growth factor, insulin-like growth factors, and granulocyte colony-stimulating factor.

The pharmaceutical compositions of the present invention may be administered by any means that achieve their intended purpose. Amounts and regimens for the administration of a HA-AP, calreticulin, or a derivative thereof, can be determined readily by those with ordinary skill in the clinical art of treating wounds.

The pharmaceutical composition of the present invention is preferably applied topically to a wound. For topical application, the compositions of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like. A most preferred vehicle is a petrolatum/lanolin vehicle.

Also suitable for topic application are sprayable aerosol preparations wherein the active ingredient, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and.or antioxidants in addition to the compounds of the invention.

For the preferred topical applications, it is preferred to administer an effective amount of a composition according to the present invention to an affected wound area, in particular the skin surface. This amount will generally range from about 0.001 mg to about 1 g per application, depending upon the area to be treated, the severity of the symptoms, and the nature of the topical vehicle employed. A preferred topical preparation is an ointment wherein about 0.01 to about 50 mg of active ingredient is used per cc of ointment base.

Alternatively, or concurrently, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the protein, peptide or derivative is contained in an amount effective to achieve its intended purpose. While individual needs vary, determination of optimal ranges of effective amounts of each component is within the skill of the art. Typical dosages comprise 0.01 to 100 mg/kg/body wt. The preferred dosages comprise 1 to 100 mg/kg/body wt.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Suitable formulations for oral administration include hard or soft gelatin capsules, dragees, pills tablets, including coated tablets, elixirs, suspensions, syrups or inhalations and controlled release forms thereof. Preparations which can be administered rectally are suppositories. Suitable injectable solutions include intravenous subcutaneous and intramuscular injectable solutions. The compositions may also be administered in the form of an infusion solution or as a nasal inhalation or spray. Suitable solutions for administration by B injection or orally, contain from about 0.01 to 99 percent, preferably from about 20 to 75 percent of active compound(s), together with the excipient. The pharmaceutical formulation for systemic administration according to the invention may be formulated for enteral, parenteral or topical administration. Indeed, all three types of formulation may be used simultaneously to achieve systemic administration of the active ingredient.

Having now generally described the invention, the same will be more readily understood through reference to the following examples which are provided by way of illustration, and are not intended to be limiting of the present invention, unless specified.

EXAMPLE I

Hyaluronan-Associated Protein in Fetal Sheep Skin

Using the fetal sheep model, the present inventors were able to obtain a large amount of fetal skin over a long gestational period (Term=145 days). As discussed previously, a large difference was found in the concentration of fetal skin hyaluronan between the "scarless period" when HA concentrations are high and the typical post-natal scarred healing period. Similarly, the present inventors' laboratories characterized the hyaluronan associated proteins of different gestational ages (Bakshandeh, N. et al. (1992) *Biochem Intl* 28:843–851).

The total protein associated with HA decreased from 42% of the dry weight at 75 days gestation when scarless healing predominates to its low of 22% at 125 days gestation scarred healing begins. Also, the protein associated with HA of fetal sheep skin varies in molecular weight depending on its gestational age. Specifically, the dominant protein profile changes at 125 days gestation, when the fetus begins to heal as an adult, from a 62 kDa peptide to a smaller protein of about 21 kDa.

Interestingly, the 62 kDa protein is only found during the period coinciding with scarless healing. Whether the 21 kDa peptide represents a post-translational modification or a degradation product of the 62 kDa protein versus a separate gene product is presently unknown.

EXAMPLE II

Dominant 62 kDa Protein Associated with Fetal Sheep Hyaluronan

Given the above data, the present inventors extracted and highly purified early gestational fetal sheep hyaluronan and associated proteins and confirmed the 62 kDa fetal hyaluronan associated protein as the dominant band in a silver stained SDS-PAGE gel.

EXAMPLE III

In Vivo Wound Healing Assay

The present inventors developed an in vivo wound healing assay in the rat. Incisional or excisional wounds were made on the dorsa of rats and were treated with HA-AP or corresponding controls. The HA-AP treated wounds healed more quickly, with better collagen organization based on light microscopy, and an increased cellular response at the wound margin.

EXAMPLE IV

Detection of TGFβ Isoforms in Wounds
Antibody Production

Antibodies against the three mammalian isoforms of TGFβ were produced by immunization of rabbits with synthetic peptides corresponding to a part of each isoform essentially as described (Pelton, R. W. et al., 1991, *J. Cell Biol.* 115:1091–1105). The sequences of each of the three TGFβ isoforms are identical in mammals. The following amino acid residues were used: TGFβ1 and TGFβ2, residues 4–19; TGFβ3, residues 9–20. The peptides were synthesized using a 430A peptide synthesizer (incorporating the t-boc solid phase synthesis method followed by hydrofluoride cleavage. The peptides were purified by HPLC using a gradient composed of 0.1% trifluoroacetic acid and 100% acetonitrile. Each peptide (5 mg) was dissolved in 0.1M $NaHCO_3$ and coupled to keyhole limpet hemocyanin at a 1:1 (w:w) ratio. Rabbits were initially immunized with 500 µg of each peptide and subsequently boosted with 250 µg every 2.5 weeks. Antibody titer was determined by ELISA using the appropriate uncoupled peptide and alkaline phosphatase-conjugated goat anti-rabbit IgG (Promega Biotec, Madison Wis). The three antisera did not cross-react with the other two "non-specific" TGFβ peptides. Each antiserum was purified by ammonium sulfate precipitation (31.3%) followed by affinity chromatography using the respective immunogenic peptide. The peptide (8 mg) was coupled to 2 ml of Tresyl-Sepharose (Pharmacia) overnight according to manufacturer's instructions. The purified IgG was eluted with 50 mM glycine (Ph 2.5) into Tris buffer (pH 7.2) for neutralization, dialyzed against TBS (0.01M Tris, 0.15M NaCl, pH 8.0), aliquoted and stored frozen.

Western Blot Analysis

Each anti-peptide antiserum was tested for both immunoreactivity with the corresponding mature isoform of the TGFβ molecule and for cross-reactivity with each other TGFβ isoform by Western blot analysis. Recombinant human TGFβ1 and TGFβ3, and native porcine TGFβ2, were reduced with 0.1M dithiothreitol, subjected to SDS-PAGE using a gradient polyacrylamide gel of 10–20% and subsequently transferred to nitrocellulose membrane for 1 hr at 1 V using the Biorad Miniblot System (Bio-Rad, Cambridge, Mass.). The membranes were blocked with 3% nonfat dry milk in TBS for 1 hr and directly incubated overnight in purified an anti-peptide IgG preparation in TBS containing 0.1% Tween 20 (TBST) at dilutions of 1:50 or 1:25. the membranes were washed with TBST and incubated with alkaline phosphatase-labeled goat anti-rabbit IgG at a dilution of 1:3000 for 1 hr. The blot was developed with the chromogenic substrate NBT/BCIP Promega).

Immunohistochemistry

Tissues were fixed overnight in 4% paraformaldehyde/phosphate buffered saline, dehydrated in increasing concentrations of ethanol and embedded in paraffin wax. Sections of 5–7 µm were cut and floated onto coated slides. Sections were submerged in TBS/0.1% (v/v) Triton X-100 at room temperature for 15 minutes, followed by TBS for 5 min., methanol for 2 min. and methanol/0.6% (v/v) hydrogen peroxide for 30 min. Slides were subsequently washed at room temperature in methanol for 2 min., TBS for 5 min. and thrice in TBS/0.1% (w/v) bovine serum albumin (BSA) for 3 min. After treatment with hyaluronidase (1 mg/ml in 100 mM sodium acetate, 0.85% NaCl), and three washes in TBS/0.1% BSA, excess protein was blocked with 5% normal swine serum in TBS/0.5% BSA for 15 min. at room temperature.

Tissue sections were incubated with primary antibody at a concentration of 2.5 µg/ml overnight at 4° C. C.control slides were incubated with either an IgG fraction of normal rabbit serum at 5 µg/ml (diluted in TBS containing 5% swine serum and 0.1% BSA) or without primary antibodies. Tissues were then washed in TBS/0.1% BSA and incubated for 60 min. at room temperature with biotinylated swine anti-rabbit second antibody in TBS/0.1% BSA. After washes with this buffer, the sections were exposed to avidin-biotin complex for 60 min at room temperature and again washed in TBS/0.1% BSA. Slides were reacted with 0.05% diaminobenzidine in 50 mM Tris-HCl (pH 7.4) with 0.1% hydrogen peroxide for 5 min and counterstained in hematoxylin.

Results

Western blot analysis showed that each of the three anti-TGFβ isoform antibodies was specific for its particular isoform and did not react with the other two TGFβ isoforms.

Immunohistochemical staining for the three mammalian TGFβ isoforms the rabbit polyclonal antibodies described above revealed a differential expression wounds treated with HA-AP compared to control wounds (See, also, Cabrera R. C. et al. (1993) *Plast Surg Res Council*).

The results, are summarized in tabular form in FIGS. 1 and 2. Briefly, in unwounded sheep skin, TGFβ1 was concentrated in the stratum corneum of the epidermis, while TGFβ2 and TGFβ3 were concentrated in the strata granulosum, spinosum, and basalis. In the dermis, there was no staining with the ant-TGFβ1 antibody, whereas anti-TGFβ2 stained mildly and anti-TGFβ3 stained moderately. Merocrine sweat glands stained moderately for TGFβ1 and TGFβ2, but only mildly for TGFβ3, while sebaceous sweat glands and hair follicles stained moderately for TGFβ2 and TGFβ3 but only mildly for TGFβ1. Endothelial cells showed little or no immunoreactivity for any of the three isoform-specific antibodies.

Wounded skin, showed a similar distribution of the immunostaining pattern in epidermis, dermis, hair follicles, and sebaceous sweat glands. However, the staining was more intense relative to unwounded skin through day 14. Interestingly, migrating epithelium arising from both the wound margin and adjacent hair follicles showed no staining of any TGFβ isoform until complete reepithelialization by day 7 in the excisional wounds and day 5 in the incisional wounds. The inflammatory exudate contained a dense band of neutrophils and macrophages which showed varying degrees of immunoreactivity from none to intense for all three TGFβ isoforms. Granulation tissue at the exudate-wound interface exhibited intense staining for all three isoforms with TGFβ3 and TGFβ2 being greater than TGFβ1. Inflammatory exudate separated from underlying granulation tissue by migrating epithelium was devoid of staining. By 21 days, staining for the three TGFβ isoforms was similar to that of unwounded skin, except for the dermis, in which new scar showed persistent immunostaining for all three isoforms, especially TGFβ3. Incisional wounds exhibited similar staining patterns.

Lack of staining in the migrating epithelium is consistent with the notion that TGFβ isoforms influence cell migration during wound repair by altering the cells' adhesive properties. Possible mechanisms include changes in integrin receptor expression and ECM modification. Increased expression of TGFβ isoforms continues in the epithelialized dermis to day 21. This persistent differential expression may be responsible for the excessive ECM and collagen found in scar tissue and the subsequent remodeling that occurs as wounds mature.

The above findings highlight the important role of peptide growth factors in the dynamic process. These results are consistent with what is known about the isoform-specific effects of TGFβ in wound repair and thus, not only demonstrate the in vivo biological activity of the HA-AP but also suggest a possible mechanism of action. Ellis and coworkers (Ellis I. et al. (1992) *J Cell Sci* 102:447–456) have demonstrated that TGFβ1 can decrease both hyaluronan production and migration into a collagen gel of fibroblasts in vitro.

Recent unpublished work by Ferguson and coworkers confirms that the addition of antibodies to TGFβ1 and TGFβ2 to adult wounds decrease scarring (Shah M. et al., supra).

The present inventors therefore envision a competitive association where, on one side, wound fibrosis and matrix accumulation is enhanced by TGFβ1 and TGFβ2 as they decrease hyaluronan production in the ECM thereby exposing hyaluronan associated proteins to proteases in the wound fluid. On the other side, collagen and matrix organization is improved as hyaluronan protected associated proteins downregulate TGFβ1 and TGFβ2 and up-regulate TGFβ3.

It is therefore postulated that the hyaluronan of the HA-AP complex protects the associated proteins from degradation, and the hyaluronan associated peptides effect growth factor expression and collagen organization and therefore can be used to modulate scarring.

EXAMPLE V

Identification of 62 kDa Hyaluronan-Associated Protein as Calreticulin

As previously stated, the present inventors isolated and purified HA-AP complex from 100-day fetal sheep skin and showed the dominant band on SDS-PAGE to be a 62 kDa polypeptide.

An N-terminal amino acid sequence analysis was performed using the electroblot method permitted determination of the first 15 residues. Comparison to known protein sequences revealed that calreticulin was the only protein with an identical N-terminus. Calreticulin is an intra-endoplasmic reticulum low affinity high capacity calcium binding protein found in non-skeletal muscle cells which shows remarkable homology between mammalian species.

These results indicate a role for calreticulin in wound healing since it is known to bind certain α subunits of integrins, the cell surface proteins mediating many cell-cell and cell-matrix interactions during wound repair.

Despite the fact that calreticulin is thought to be localized in the endoplasmic reticulum, a pool of 60 kDa peptides homologous to calreticulin was found free in the soluble cytosol, indicating the feasibility of an interaction of this peptide with the integrin α subunits (Rojiani M. V. et al. (1991) *Biochem* 30:9859–9866).

Furthermore, while calreticulin is immunolocalized to both the endoplasmic reticulum and nucleus in proliferating myocytes, the addition of TGFβ which induces terminal differentiation of the myocytes diminishes the intranuclear staining (Opas M. et al. (1991) *J Cell Physiol* 149:160–171). Thus, prior to terminal differentiation calreticulin is immunolocalized differently within the cell.

This behavior reminiscent of the fetal 62 kDa HA-AP which is only present early in gestation when fetal skin retains the ability to heal by regeneration but is absent by the mid-third trimester when it heals with typical post-natal scarring.

The present inventors propose that these hyaluronan associated proteins, in particular calreticulin, play a significant role in the in vivo organization of scar tissue. In the fetus, the dominant HA-AP is a 62 kDa peptide, calreticulin, which is believed to contribute to the near perfect collagen organization seen in early fetal wounds. It is proposed that the hyaluronan, although not directly responsible for the biologic effect of scarless healing, protects associated proteins from wound proteases. This is supported by the finding that selective protease digestion did not alter in vitro biological activity of HA-AP unless preceded by hyaluronidase treatment.

Thus, based on the above results and our growing understanding of fetal ECM remodeling, the present inventors conceived of the use of calreticulin in novel compositions and methods for the ultimate goal of avoiding scarring in the wound healing process.

EXAMPLE VI

Not All Fetal Tissue Wounds Heal without Scarring

Bilateral incisional diaphragmatic wounds were created in 100 day gestation fetal lambs (term=145 days). The right thoracotomy wound was closed to exclude amniotic fluid. In contrast, an Eloesser flap was created at the left thoracotomy site, thus permitting the left diaphragmatic wound to be continually bathed in amniotic fluid (FIG. 3).

Wounds were harvested at one, two, seven, or 14 days following wounding and analyzed by light microscopy and immunohistochemistry with antibodies to collagen types I, III, IV, and VI.

Whether bathed in or excluded from amniotic fluid, the mesothelial-lined diaphragm healed with scar formation and without evidence of muscle regeneration. Interestingly, wounds exposed to amniotic fluid were covered by a thick fibrous peel of collagen similar to that seen in gastroschisis bowel. These findings indicate that not all fetal tissues share the unique scarless healing properties of fetal skin.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of promoting the scarless healing of a wound in a subject, comprising administering to said subject in need of such treatment an amount of calreticulin effective in promoting scarless healing of wounds.

2. A method according to claim 1 wherein said method further comprises administering to said subject, in combination with said calreticulin, an effective amount of at least one other agent which promotes the healing of wounds or treats symptoms accompanying wounds.

3. A method according to claim 2 wherein said agent is selected from the group consisting of an anti-bacterial agent, an anti-vital agent, an anti-fungal agent, a local anesthetic and an analgesic.

4. A method according to claim 1 wherein said method further comprises administering to said subject, in combination with said calreticulin an effective amount of a growth factor which, when administered in combination with said calreticulin, modulates wound healing.

5. A method according to claim 1, wherein said administering is by topical application and said calreticulin is incorporated into a solid or semisolid vehicle or carrier for topical application.

6. A method for modulating the expression of transforming growth factor-β isoforms in the healing tissue of a wound in a subject, such that transforming growth factor-β3 expression is enhanced and transforming growth factor-β1 expression and transforming growth factor-β2 expression are inhibited, which method comprises administering to said subject an amount of calreticulin effective in enhancing transforming growth factor-β3 and inhibiting transforming growth factor-β1 and transforming growth factor-β2.

7. A pharmaceutical composition useful in the promotion of scarless wound healing, comprising:
(a) an amount of calreticulin effective for promoting scarless wound healing; and
(b) a pharmaceutically acceptable topical carrier which is selected from the group consisting of an aerosol, a sprayable formulation admixed with a propellant, a non-sprayable formulation having a dynamic viscosity greater than water, an emulsion, a cream, an ointment, a gel, a liniment, a salve or a powder.

8. A pharmaceutical composition according to claim 7, further comprising:
(c) a growth factor which, when administered in combination with said calreticulin, modulates would healing.

9. A pharmaceutical composition according to claim 8 wherein said calreticulin is incorporated into a solid or semisolid carrier for topical administration.

10. A pharmaceutical composition according to claim 7 wherein said calreticulin is incorporated into a solid or semisolid carrier for topical administration.

11. A pharmaceutical composition according to claim 7, further comprising:
(c) at least one other agent which promotes the healing of wounds or treats symptoms accompanying wounds.

12. A pharmaceutical composition according to claim 11, wherein said agent is selected from the group consisting of an anti-bacterial agent, an anti-viral agent, an anti-fungal agent, a local anesthetic and an analgesic.

13. A pharmaceutical composition according to claim 12 wherein said calreticulin is incorporated into a solid or semisolid carrier for topical administration.

14. A pharmaceutical composition according to claim 11 wherein said calreticulin is incorporated into a solid or semisolid carrier for topical administration.

* * * * *